US006831781B2

(12) United States Patent
Tearney et al.

(10) Patent No.: US 6,831,781 B2
(45) Date of Patent: Dec. 14, 2004

(54) CONFOCAL MICROSCOPY WITH MULTI-SPECTRAL ENCODING AND SYSTEM AND APPARATUS FOR SPECTROSCOPICALLY ENCODED CONFOCAL MICROSCOPY

(75) Inventors: Guillermo J. Tearney, Cambridge, MA (US); Brett E. Bouma, Quincy, MA (US); Robert H. Webb, Lincoln, MA (US); Constantinos Pitris, Nicosia (CY); Millen Shishkov, Newline Ruse (BG)

(73) Assignee: The General Hospital Corporation, Boston, MA (US)

( * ) Notice: Subject to any disclaimer, the term of this patent is extended or adjusted under 35 U.S.C. 154(b) by 87 days.

(21) Appl. No.: 09/999,182

(22) Filed: Nov. 29, 2001

(65) Prior Publication Data

US 2002/0122246 A1 Sep. 5, 2002

Related U.S. Application Data

(63) Continuation-in-part of application No. 09/622,971, filed as application No. PCT/US99/04356 on Feb. 26, 1999, now Pat. No. 6,341,036.
(60) Provisional application No. 60/076,041, filed on Feb. 26, 1998.

(51) Int. Cl.[7] .............................................. G02B 21/06
(52) U.S. Cl. ...................................... 359/385; 359/368
(58) Field of Search ................................ 359/368, 385, 359/389, 196, 209

(56) References Cited

U.S. PATENT DOCUMENTS

| 4,965,441 | A | | 10/1990 | Picard |
| 5,127,730 | A | | 7/1992 | Brelje et al. |
| 5,248,876 | A | | 9/1993 | Kerstens et al. |
| 5,304,810 | A | | 4/1994 | Amos |
| 5,450,203 | A | | 9/1995 | Penkethman |
| 5,459,325 | A | | 10/1995 | Hueton et al. |
| 5,526,338 | A | | 6/1996 | Hasman et al. |
| 5,565,986 | A | | 10/1996 | Knuttel |
| 5,600,486 | A | | 2/1997 | Gal et al. |
| 5,698,397 | A | | 12/1997 | Zarling et al. |
| 5,785,651 | A | | 7/1998 | Kuhn et al. |
| 5,887,009 | A | * | 3/1999 | Mandella et al. ............... 372/6 |
| 6,111,645 | A | | 8/2000 | Tearney et al. |
| 6,166,373 | A | | 12/2000 | Mao |
| 6,341,036 | B1 | * | 1/2002 | Tearney et al. ............. 359/368 |
| 6,469,846 | B2 | | 10/2002 | Ebizuka et al. |

* cited by examiner

*Primary Examiner*—Mark A. Robinson
(74) *Attorney, Agent, or Firm*—Frommer Lawrence & Haug LLP; Thomas J. Kowalski; Amy Leahy

(57) ABSTRACT

A scanning confocal microscopy system and apparatus, especially useful for endoscopy with a flexible probe which is connected to the end of an optical fiber (9). The probe has a grating (12) and a lens (14) which delivers a beam of multi-spectral light having spectral components which extend in one dimension across a region of an object and which is moved to scan in another dimension. The reflected confocal spectrum is measured to provide an image of the region.

48 Claims, 23 Drawing Sheets

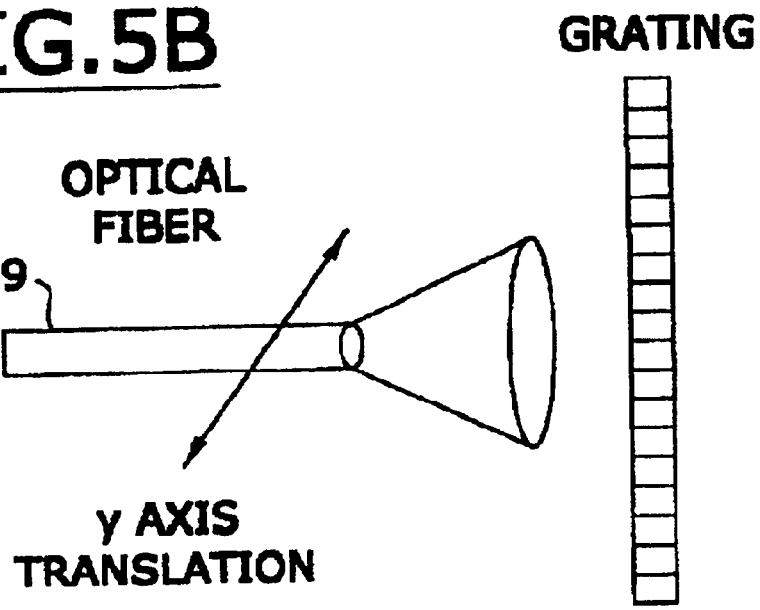

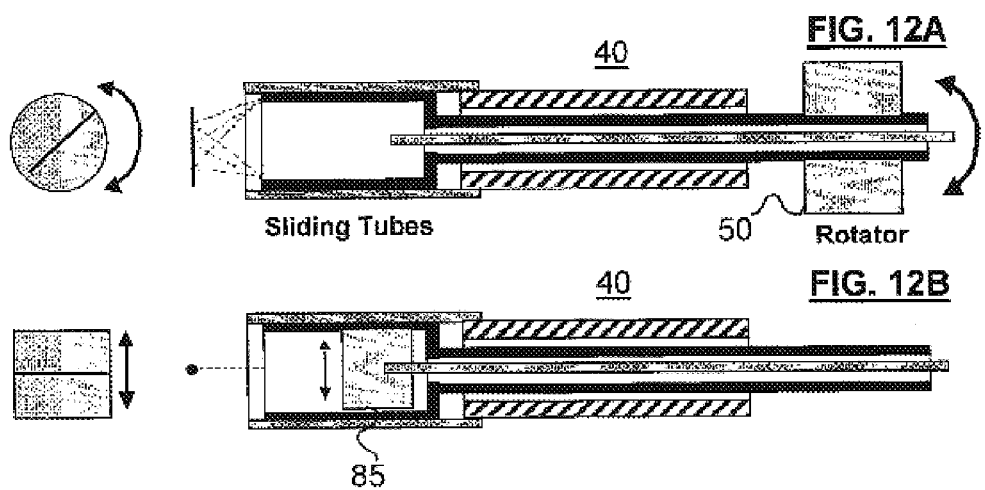

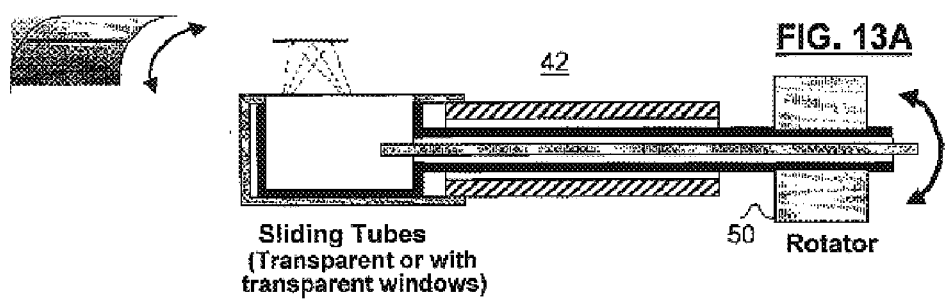
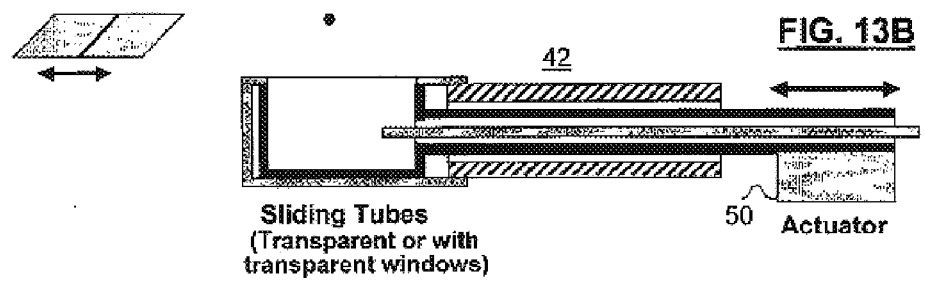

Tissue

Actuator — 95
(Piezoelectric, Mechanic Pneumatic,
Acousto-optic, Electro-optic, etc.)

Tissue

100 Transparent Balloon

105

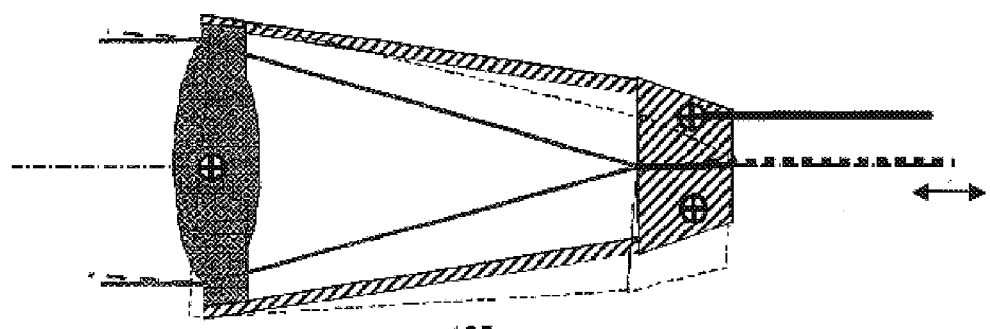
105
FIG. 19A
FIG. 19B
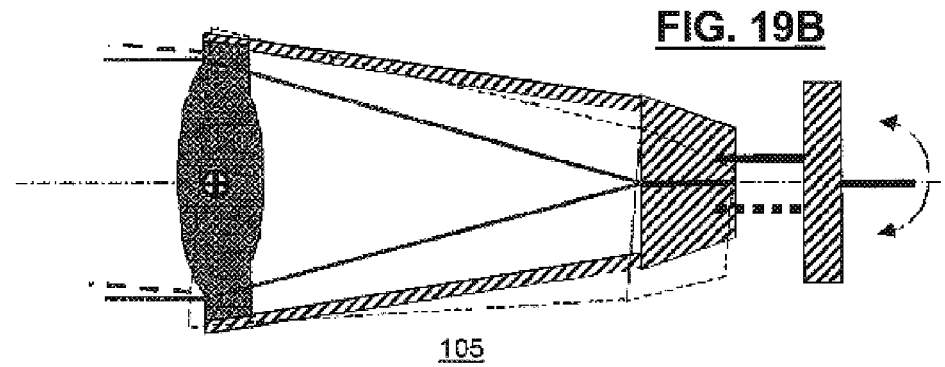
105

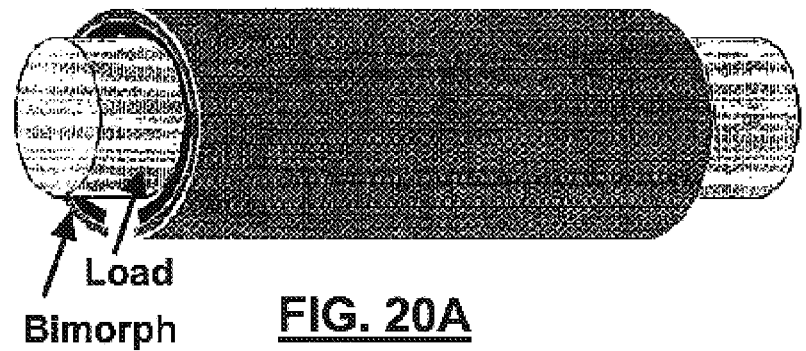
FIG. 20A Load, Bimorph
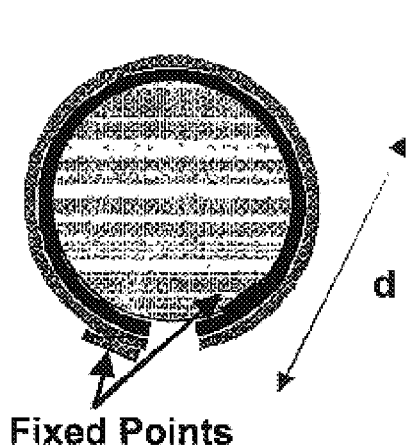
FIG. 20B Fixed Points
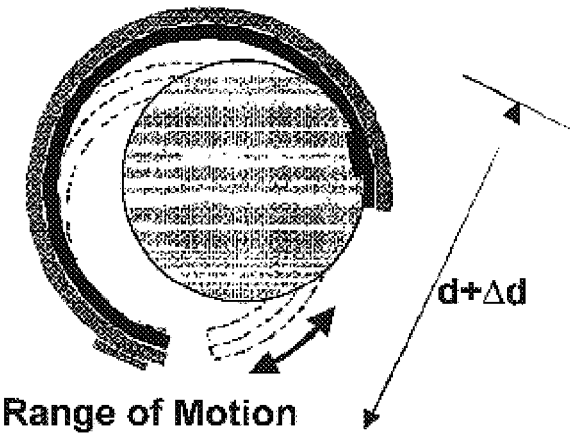
FIG. 20C Range of Motion

CONFOCAL MICROSCOPY WITH MULTI-SPECTRAL ENCODING AND SYSTEM AND APPARATUS FOR SPECTROSCOPICALLY ENCODED CONFOCAL MICROSCOPY

This is a continuation-in-part application of U.S. application Ser. No. 09/622,971, filed Aug. 24, 2000, now U.S. Pat. No. 6,341,036 which is a national stage application of International Application No. PCT/US99/04356, filed Feb. 26, 1999, claiming priority to U.S. Provisional Application No. 60/076,041, filed Feb. 26, 1998, the contents of which are incorporated herein by reference.

BACKGROUND OF THE INVENTION

The present invention relates to systems (method and apparatus) for confocal microscopy for the examination or imaging of sections of a specimen of biological tissue, and particularly to such systems using multi-spectral illumination and processing of multi-spectral light.

Medical imaging technology has advanced over the last twenty years to provide physicians with indispensable information on the macroscopic anatomy of patients. Imaging techniques such as radiography, magnetic resonance imaging, computed tomography, and ultrasound non-invasively allow investigation of large-scale structures in the human body with resolutions ranging from 100 $\mu$m to 1 mm. However, many disease processes, such as the detection of early stages of cancer, higher resolution is necessary for proper diagnosis. In addition, clinical procedures such as screening for carcinoma and the surgical detection of tumor margins require higher resolution diagnostic imaging methods.

SUMMARY OF THE INVENTION

To address these and other clinical problems in situ, a non-invasive imaging technology with a resolution that approaches standard histopathology must be used. One promising potential noninvasive imaging modality is a form of light microscopy known as reflectance confocal microscopy.

Currently, the use of fast scanning confocal microscopy is limited to accessible surfaces of the skin and the eye. The reason for this is that the only reliable methods for optical scanning must be performed in free space. In addition, the size of these optical scanners prohibit their use in small probes such as endoscopes or catheters. It is a feature of the invention to miniaturize the fast scanning mechanism and increase the number of medical applications of confocal microscopy to include all surfaces of the body, gynecologic applications, probe-based applications, and internal organ systems.

Multi-spectral light was proposed for use in confocal microscopy, but only for imaging vertically-spaced regions of a body under examination. See B. Picard, U.S. Pat. No. 4,965,441, issued Oct. 25, 1990. An interferometer using a grating to obtain multi-spectral light which is resolved in the interferometer to obtain a spectroscopic image is disclosed in A. Knuttal, U.S. Pat. No. 5,565,986, issued Oct. 15, 1996. A lens having a color separation grating which obtains a multi-spectral light is disclosed in U.S. Pat. No. 5,600,486, issued Feb. 4, 1997. Such multi-spectral proposals are not effective for high resolution imaging using a compact, flexible probe. A confocal microscope system according to this invention can be miniaturized and incorporated into a compact probe. In addition, by allowing light delivery through a single optical fiber, the probe may also be easily incorporated into catheters or endoscopes. Thus, a confocal microscope in accordance with the invention allows imaging of all accessible surfaces of the body and increases the biomedical applications of confocal microscopy by an order of magnitude.

Briefly described, a confocal microscopy system embodying the invention illuminates a region of interest in a body into which said probe may be inserted with a confocal spectrum extending along one dimension. Optics in said probe or physical movement of said probe enabled by attachment thereto of a flexible light conductive member (which may be an optical fiber), enables scanning of said spectrum along one or two additional dimensions thereby providing for two or three dimensional imaging of the region. The reflected confocal spectrum may be detected or decoded spectroscopically, preferably with a heterodyne detection mechanism which may be implemented interferometrically.

The following are hereby incorporated by reference:

Corcuff, P. and J. L. Leveque, In vivo vision of the human skin with the tandem scanning microscope. Dermatology, 1993. 186: p. 50–54;

Rajadhyaksha, M., et al., In vivo confocal scanning laser microscopy of human skin: Melanin provides strong contest. J. Invest. Derm., 1995. 104: p. 946;

Webb, R. H., Scanning laser ophthalmoscope, in Noninvasive diagnostic techniques in ophthalmology, B. R. Masters, Editor. 1990, Springer-Verlag: New York; and Tearney, G. J., R. H. Webb, and B. E. Bouma, Spectrally encoded confocal microscopy. Optics Letters, 1998. 23(15): p. 1152–1154.

In order to image the majority of accessible epithelial tissues in vivo three important requirements must be met. First, a focused beam must be scanned across the specimen. Second, the image acquisition time has to be sufficiently short to prevent motion artifacts. Finally, the device must be small enough to be incorporated into and endoscope or catheter. Techniques such as tandem scanning and laser scanning confocal microscopy have been developed address the rapid beam scanning requirements for an in vivo confocal imaging system. However, in these methods, high speed scanning is obtained through the use of large mechanical devices that are not easily miniaturized. As a result, the utility of these techniques is primarily limited to the fields of dermatology and ophthalmology. A promising new a fiber optic based technique, spectrally encoded confocal microscopy ("SECM"), has recently been demonstrated. This technique allows reflectance confocal microscopy to be performed through a compact probe, such as a catheter or endoscope. SECM uses wavelength division multiplexing ("WDM") to encode one-dimensional spatial information reflected from the sample. The fast scanning axis is replaced by a series of focused points with each location being represented by a different wavelength of light. The remittance as a function of spatial position is determined by measuring the spectrum of the reflected light (FIG. 8). A two-dimensional image is created by scanning the wavelength-encoded axis by slow mechanical motion of the probe. Thus, endoscopic devices embodying the invention allow SECM imaging of a variety of tissues and organs either integrated with standard endoscopes or as stand-alone devices.

In accordance with an embodiment of the invention, a device capable of performing in vivo endoscopic confocal microscopy is provided. Such a device could potentially provide physicians with a tool for performing non-invasive subcellular diagnostic imaging in internal organ systems. Such a modality would have significant long-term impact in its ability to enable a variety of clinical applications including cancer screening or biopsy guidance and intraoperative tumor or other tissue identification. A device embodying the present invention could enable in vivo endoscopic confocal microscopy imaging and potentially allow diagnosis of critical tissues of interest. Despite the added complexity, such a device could provide access to otherwise inaccessible tissues therefore significantly enhancing the value of confocal microscopy as a diagnostic tool.

BRIEF DESCRIPTION OF THE DRAWINGS

The invention will be more apparent from the following drawings wherein

FIGS. 5A–D are schematic diagrams showing: (a) image formation; (b) translation of the optical fiber in the y direction; (c) rotation of the optical fiber in the forward firing mode; and (d) rotation of the optical fiber in the side firing mode;

FIGS. 12A and 12B illustrate slow axis scanning for the forward-imaging probe of FIG. 9A in accordance with respective embodiments of the invention;

FIGS. 13A and 13B illustrate slow axis scanning for the side-imaging probe of FIG. 9B in accordance with respective embodiments of the invention;

FIGS. 19A and 19B illustrate the slow scanning mechanisms of FIGS. 18A and 18B, respectively; and FIGS. 20A, 20B, and 20C are diagrams illustrating a slow scanning mechanism using a circular piezoelectric bimorph in accordance with an embodiment of the invention.

DETAILED DESCRIPTION OF THE PREFERRED EMBODIMENTS

Figure 1:
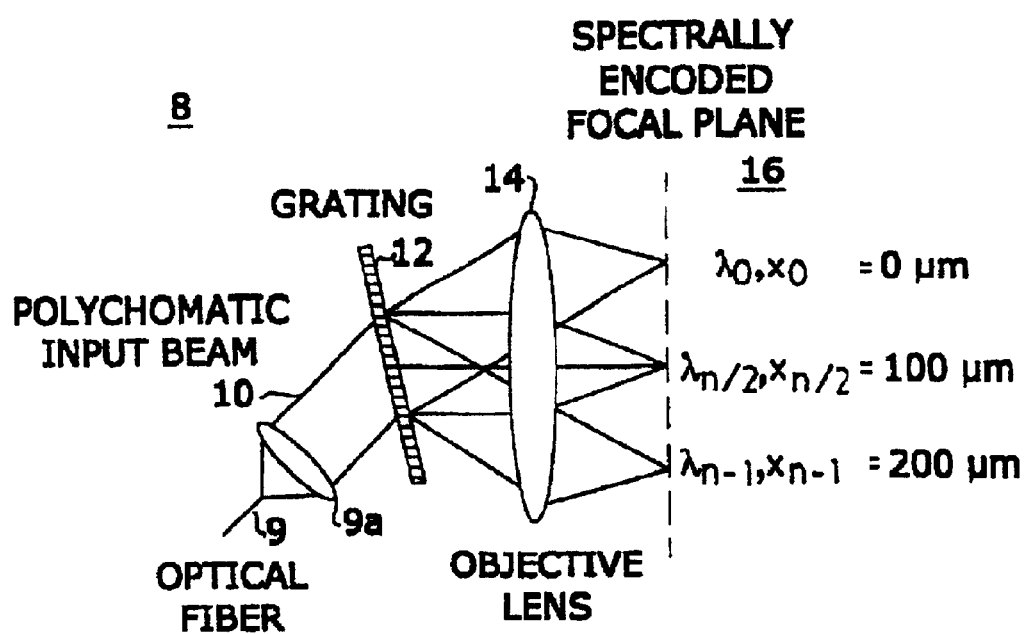
FIG. 1 is a schematic diagram of a spectrally encoded confocal probe in accordance with the invention where specific wavelengths are shown for illustrative purposes, their exact values depending on the optical parameters of the system.

Referring now to the figures, multi-spectral encoding for confocal microscopy uses a broad bandwidth source 10 as the input to the microscope. In the probe 8 of the microscope, the source spectrum provided via an optical fiber 9 is dispersed by a grating 12 and focused by an objective lens 14 onto the sample 16. A lens 9a is preferably disposed between the optical fiber 9 and the grating 12 to collimate the light from the optical fiber, as shown in FIG. 1, however, lens 9a may be removed. The spot for each wavelength is focused at a separate position, x, on the sample (FIG. 1). The reflectance as a function of transverse location is determined by measuring the reflected confocal spectrum from the sample 16 returned from probe 8.

The number of wavelengths or points that may be resolved is determined by:

$$\frac{\lambda}{\partial \lambda} = mN, \quad (1)$$

where $\lambda$ is the center wavelength, $\partial \lambda$ is the bandwidth of the spectrum, N is the number of lines in the grating 12 illuminated by the polychromatic input beam 10, and m is the diffraction order. If the total bandwidth of the source is $\Delta\lambda$, the number of resolvable points, n is defined by:

$$n = \frac{\Delta\lambda}{\partial\lambda}, \quad (2)$$

Figure 2:
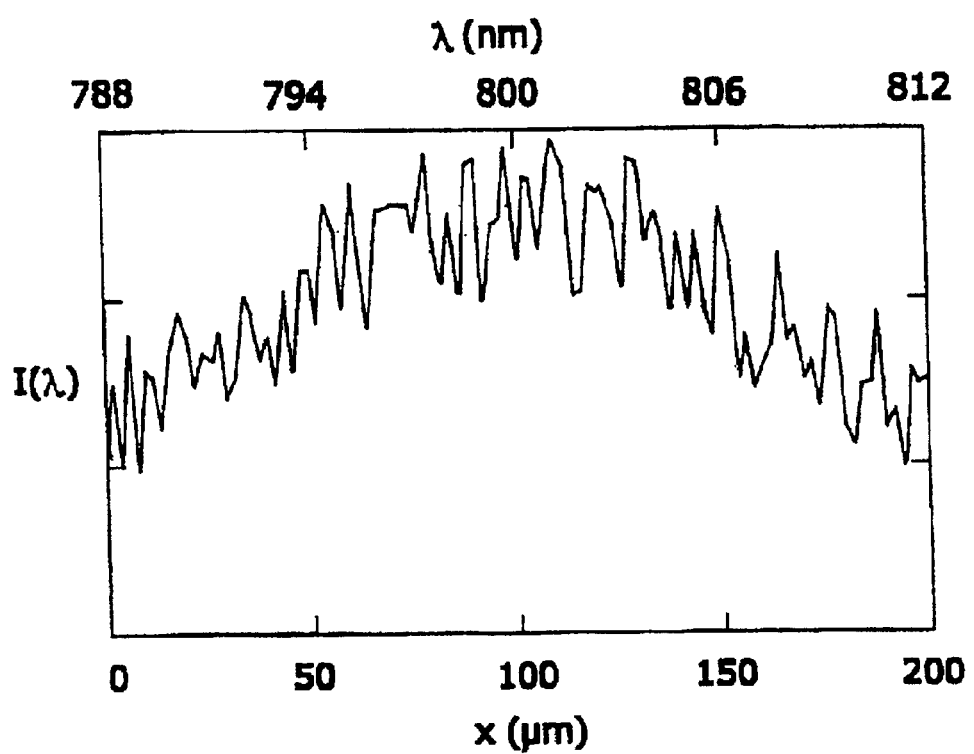
FIG. 2 is a plot of spectrally encoded light obtained by confocal detection using direct spectral detection in accordance with this invention, where different wavelengths are detected by turning the spectrometer grating.

For an input source with a center wavelength of 800 nm, a bandwidth of 25 nm, an input spot diameter of 5 mm, a diffraction grating of 1800 lines/mm and a diffraction order of 1, n=281 points may be resolved by the spectrally encoded confocal system (FIG. 2). The parameters used in this example may be found in common, inexpensive optical components. The number of points may be increased by simply increasing the input spot diameter or the bandwidth of the source. Increasing the spot diameter increases the resultant probe diameter. Increasing the bandwidth of the source could be accomplished by using a broader bandwidth superluminescent diode, a rare earth doped fiber superfluorescent source, or a solid state modelocked laser.

Figure 3:
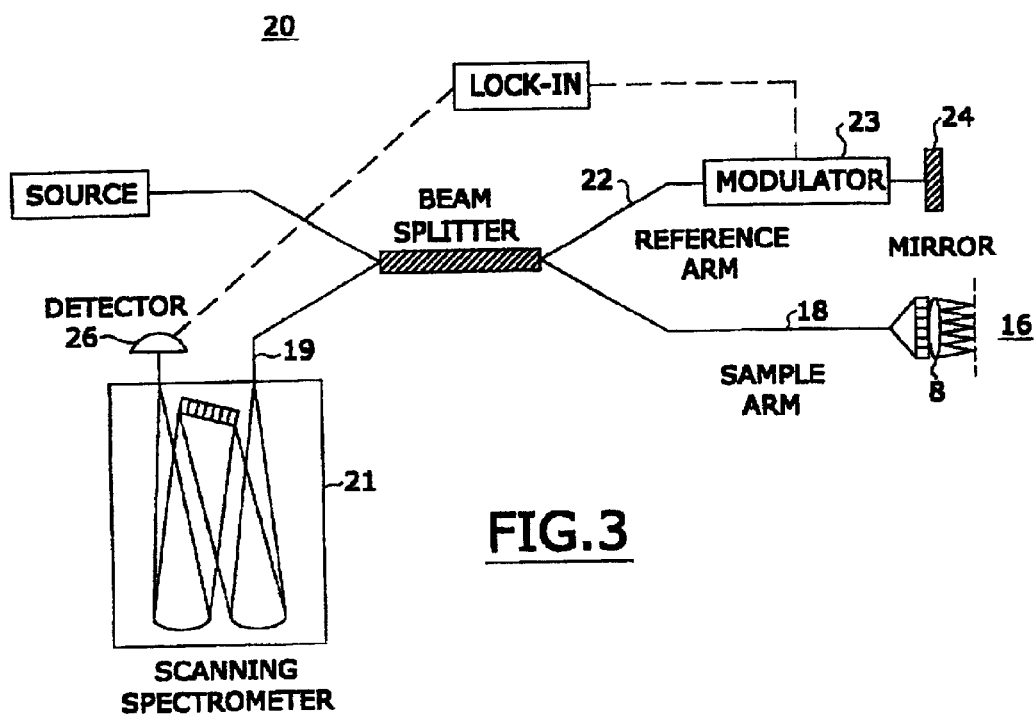
FIG. 3 is a schematic diagram showing a system embodying the invention using a spectrometer for measurement of the spectrum, I($\lambda$), which corresponds to reflectance from different transverse locations, x, on the specimen.

Consider next the multi-spectral process. First, consider direct spectral measurement. The reflectance from the sample 16 as a function of transverse location is determined by measuring the reflected confocal spectrum from the sample arm 18. The spectrum may be measured efficiently by incorporating the probe 8 in the sample arm of a Michelson interferometer 20 (FIG. 3) and detecting the light transmitted through a high resolution spectrometer 21 at the output port 19 of the interferometer. Thus, each wavelength measured corresponds to a separate position, x, on the sample (FIG. 3). The advantage to this method over traditional real time confocal microscopy is that the fast axis scanning (~15 kHz) may be performed external to the probe 8 by the spectrometer 21 with approximately 0.1 nm spectral resolution for the parameters given above, well within reach of high quality spectrometers.

High sensitivity may be achieved through the use of heterodyne detection. If the reference arm 22 is modulated, such as by modulator 23 with mirror 24 (FIG. 3), the interference of light from the sample arm 18 and the reference arm 22 will also be modulated.

High signal-to-noise ratios may be then achieved by lock-in detection on the reference arm modulation frequency of detector 26.

Figure 4:
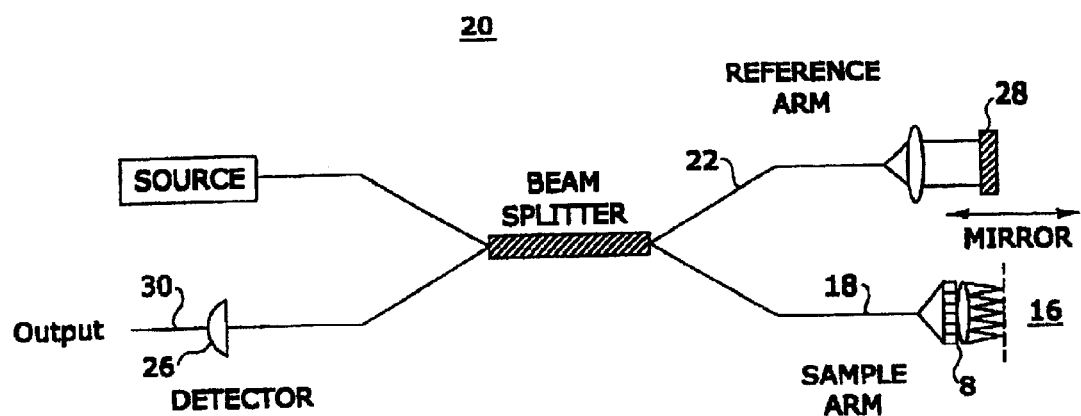
FIG. 4 is a schematic diagram of a system embodying the invention having spectrally encoded confocal detection using interference spectroscopy.

Another method for measuring the spectrum is interference or Fourier transform spectroscopy. This may be accomplished by inserting a linearly translating mirror 28 in the reference arm 22 and measuring the cross-correlation output 30 from the interference spectrometer due to the interference of the reflected light from the sample and reference arms 18 and 22, respectively (FIG. 4). The advantages to this type of spectroscopic detection include the ability to achieve higher spectral resolutions than direct detection methods, efficient use of the returned light, inherent modulation of the reference arm 22 by the Doppler shift of the moving mirror 28, and the capability to extract both reflectance and phase data from the sample 16. The ability to extract phase data from the sample may allow detection of refractive index as a function of transverse position, x, which is useful to reveal the molecular composition of the sample as well as provide an additional source of image contrast other than the reflectivity of the sample specimen 16. Finally, interferometric detection has the potential to allow elimination of high order multiple scattering from the confocal signal by coherence gating.

Figure 5A:
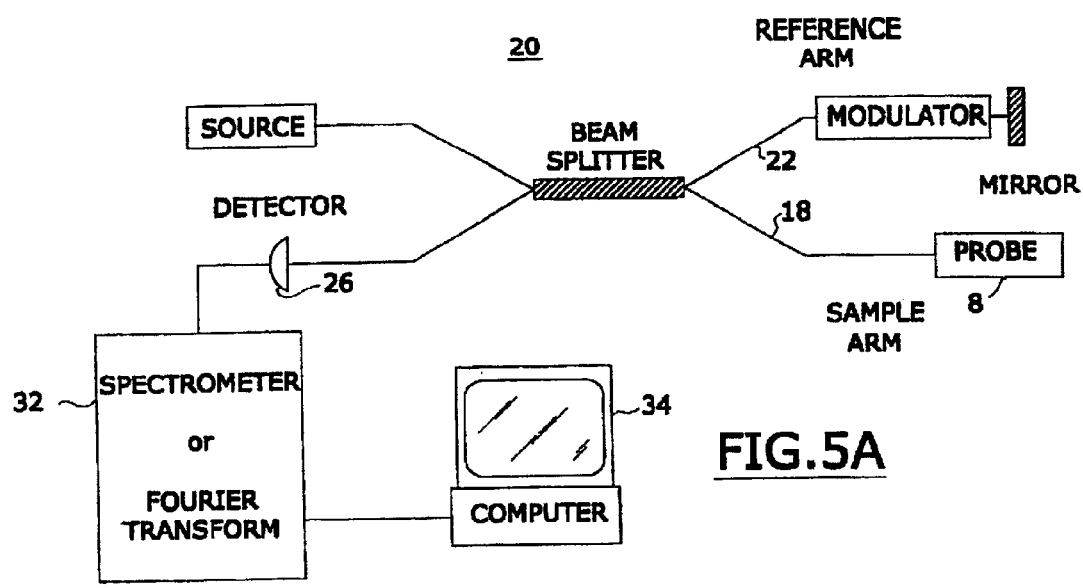
Figure 5C:
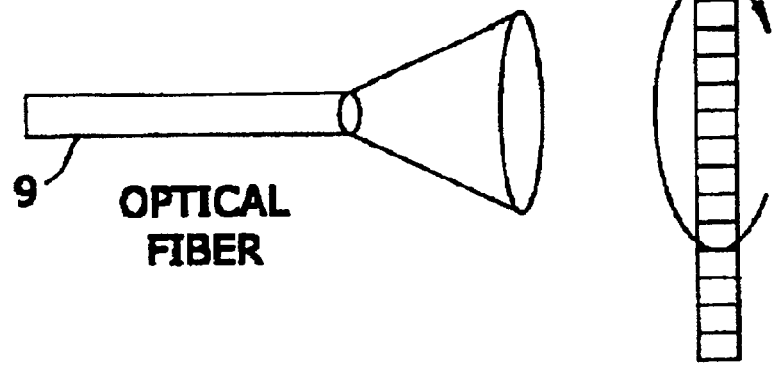
Figure 5D:
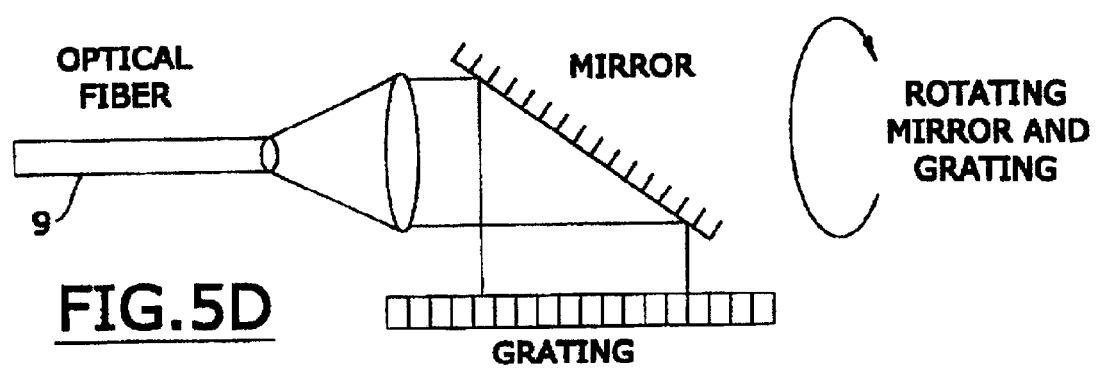
Figure 6:
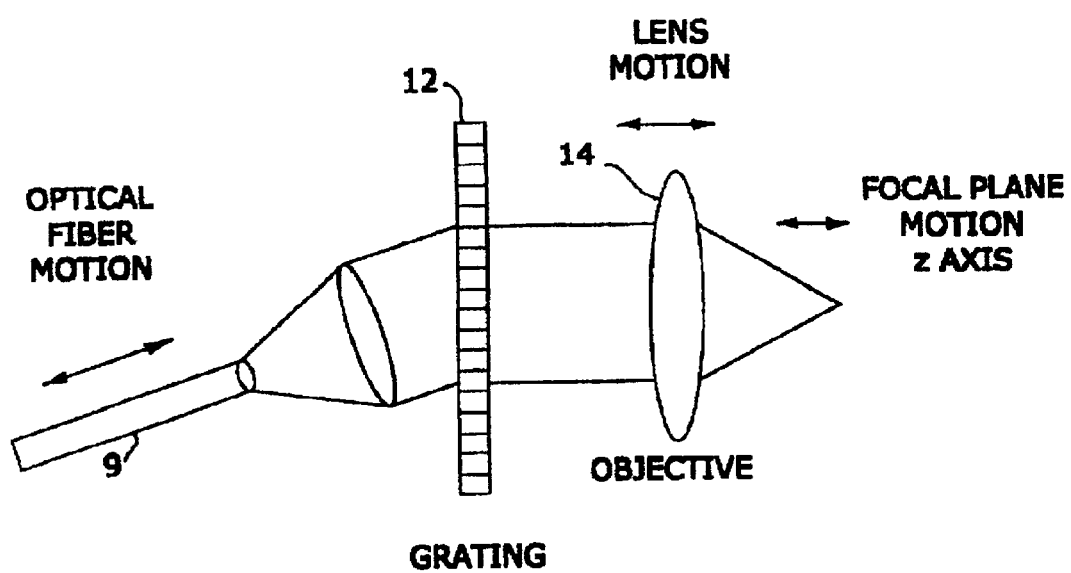
FIG. 6 is a schematic diagram showing cross-sectional image formation by scanning the optical fiber or the objective lens along the z axis using a system embodying the invention.
Figure 7:
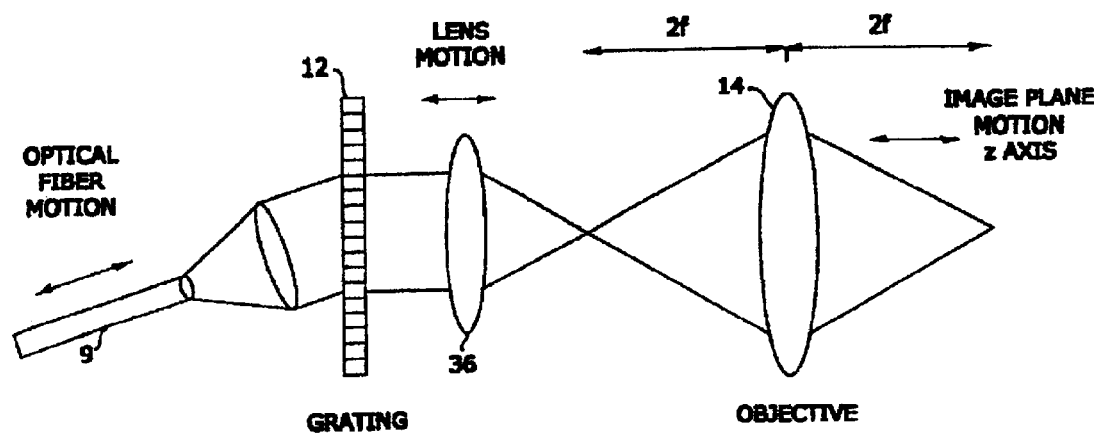
FIG. 7 is another schematic diagram of a system embodying the invention wherein optical zoom is achieved by moving the focus of an intermediate lens in and out of the image plan of the objective.

Consider finally image formation. The multi-spectral encoding of the transverse location, x, allows the performance of a one-dimensional raster scan. To obtain an image, a scan of another axis must be performed, which is usually slower. Methods of accomplishing this slow scanning of the y axis include moving the optical fiber 9 in the y direction (FIG. 5B), or rotating the entire probe 8 around the optical fiber axis either in a forward scanning configuration (FIG. 5C) or a side-firing configuration (FIG. 5D). Cross-sectional images may be created by scanning the optical fiber 9 or the objective lens 14 along the z axis (FIG. 6). Finally, a zoom mode may be created by scanning the optical fiber 9 (or another lens 32 between grating 12 and objective lens 14), in and out of the image plane of the objective lens (FIG. 7). Both linear motion along the y or z axis and rotation are easily accomplished in a compact probe by use of piezoelectric transducers. As shown in FIG. 5A, signals may be received by a computer 34 from spectroscopic detector 32 by a spectrometer (such as described in connection with FIG. 3) or Fourier transform (such as described connection with FIG. 4) representing an image of a microscopic section of the sample, and the image displayed on a display coupled to the computer.

Figure 8:
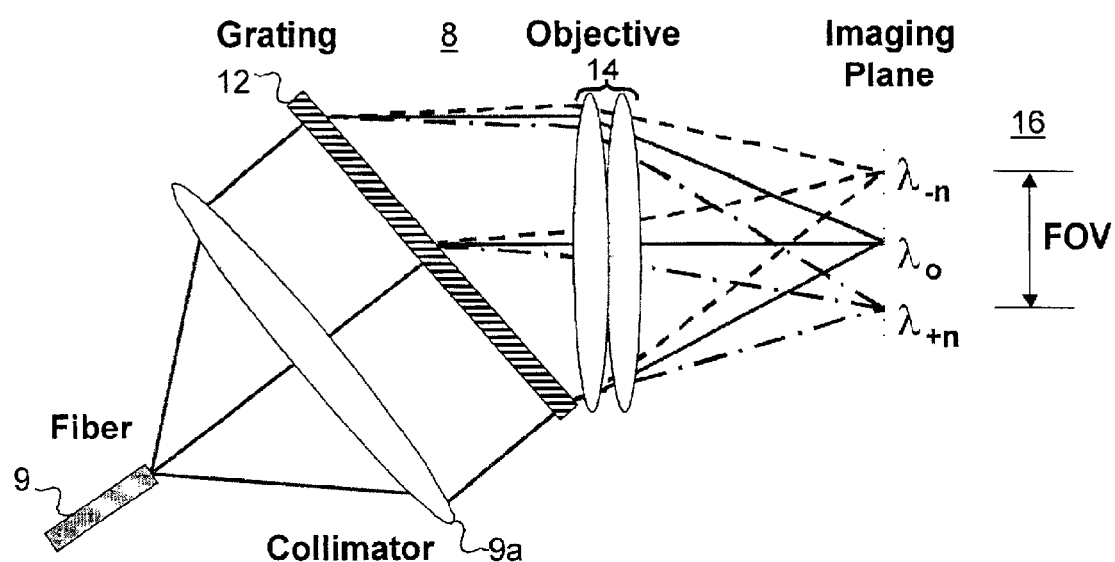
FIG. 8 is a diagram showing the basic principles of a spectrally encoded confocal probe in accordance with an embodiment of the invention.

As described before, spectrally encoded confocal microscopy ("SECM") allows reflectance confocal microscopy to be performed through a compact probe, such as a catheter or endoscope. SECM uses wavelength division multiplexing ("WDM") to encode one-dimensional spatial information reflected from the sample. The fast scanning axis is replaced by a series of focused points with each location being represented by a different wavelength of light. The remittance as a function of spatial position is determined by measuring the spectrum of the reflected light (FIG. 8). A two-dimensional image is created by scanning the wavelength-encoded axis by slow mechanical motion of the probe. Thus, endoscopic devices embodying the invention allow SECM imaging of a variety of tissues and organs either integrated with standard endoscopes or as stand-alone devices.

FIG. 8 illustrates the basic optical properties and components of SECM probe 38 in accordance with an embodiment of the invention. SECM probe 38 includes elements similar to those of probe 8 shown in FIG. 1 and is denoted by like reference numerals for such elements. Description of these elements has been provided above with reference to FIG. 1 and will not be repeated here. As shown in FIG. 8, objective lens unit 14 may comprise one or more (e.g., two) lenses for focusing the source spectrum from fiber 9 dispersed by grating 12 onto an imaging plane at sample 16. It is noted that the imaging plane may be focused on any surface, within any portion, and the like, of sample 16. The range of the source spectrum dispersed by grating 12 and focused by objective lens unit 14 on the imaging plane (from $\lambda_{-n}$ through $\lambda_0$ to $\lambda_{+n}$) may form a field of view ("FOV") of the SECM probe 38. The range may be focused onto a first dimension, which may extend in any direction (i.e., a vector along the first dimension may point in said any direction), including, a longitudinal direction (or along the "z-axis" as shown in FIG. 6), a direction that is substantially transverse to the longitudinal direction, any direction therebetween, and so forth. For example, the first dimension may be a non-longitudinal dimension extending in any non-longitudinal direction (i.e., not on the "z-axis" shown in FIG. 6). It is noted, of course, that a dimension, such as the first dimension, may extend in two opposite directions. The range may be focused onto a straight line along the first dimension, a curved line, around a circle, around an ellipse, or onto any range of points. The focused range may be scanned in another direction, i.e., different from that of a vector along the first dimension (e.g., in a direction that is transverse to a vector along the first dimension, and the like), along a second dimension (which may also be referred to as "slow axis") to form the imaging plane. The spectrum may also be scanned around an axis that extends in another direction, i.e., different from that of a vector along the first dimension, to form the imaging plane.

Figure 9:
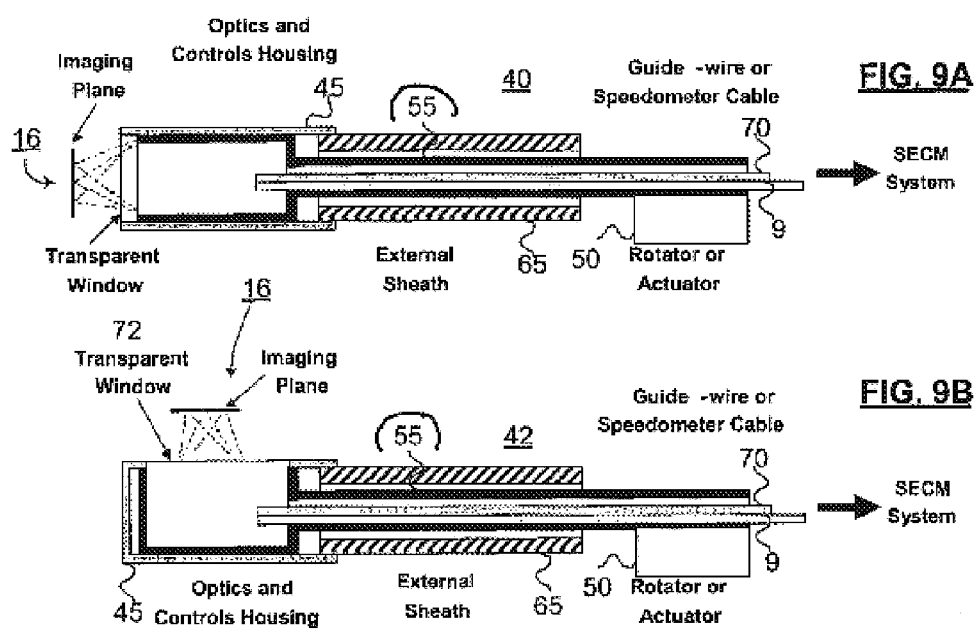
FIGS. 9A and 9B depict: (a) a SECM forward-imaging probe; and (B) a SECM side-imaging probe embodying the invention.

FIG. 9A shows an example of the construction, as well as the basic mechanics, of a forward-imaging SECM probe/catheter 40 according to an embodiment of the present invention. As shown therein, forward-imaging SECM probe/catheter 40 may include a an optics and control housing 45, a rotator/actuator 50, and an inner core 55, which may contain a fiber optic element (e.g., fiber 9) that is coupled to a SECM system (e.g., as shown in FIGS. 3, 4, and 5A) at the proximal end and focuses and redirects light at the distal end (FIG. 9A). Optical components (or "distal optics") similar to those of probe 8 or 38 may be enclosed in optics and controls housing 45 within inner core 55. Accordingly, as described above, two-dimensional imaging can be achieved either by rotating or translating the inner core 55 (and thus the optical components within) or deflecting the beam. An example of optical components, and characteristics thereof, that are specifically designed for forward-imaging SECM probe/ catheter 40 according to an embodiment of the invention will be described in further detail below with reference to FIG. 10. The inner core may be enclosed in a sheath 65 that may accommodate a guidewire 70 as well as electrical or mechanical/pneumatic connections to the distal optics. A transparent window 72 may be provided to protect the optical components from moisture, dust, and so forth. FIG. 9B shows an example of the construction, as well as the basic mechanics, of a side-imaging SECM probe/catheter 42 according to an embodiment of the present invention. As shown therein, side-imaging SECM probe/catheter 42 may include elements that are similar to those of forward-imaging SECM probe. Description of these elements will not be repeated here. However, it is noted that the imaging plane (at sample 16) of side-imaging SECM probe/catheter 42 may be at an angle to the axis of the probe/catheter 42, whereas the imaging plane of forward-imaging SECM probe/catheter 40 may be extended from the distal end of optics and controls housing 45. Thus, depending on the type of sample 16 (e.g., the surrounding structure) to be imaged, probe/catheter 40 and/or probe/catheter 42 may be used. As will be described below with reference to FIG. 11, the optical components of optics and controls housing 45 in side-imaging SECM probe/catheter 42 may be adjustable to focus the imaging plane to any angle from the axis of the probe.

Figure 10:
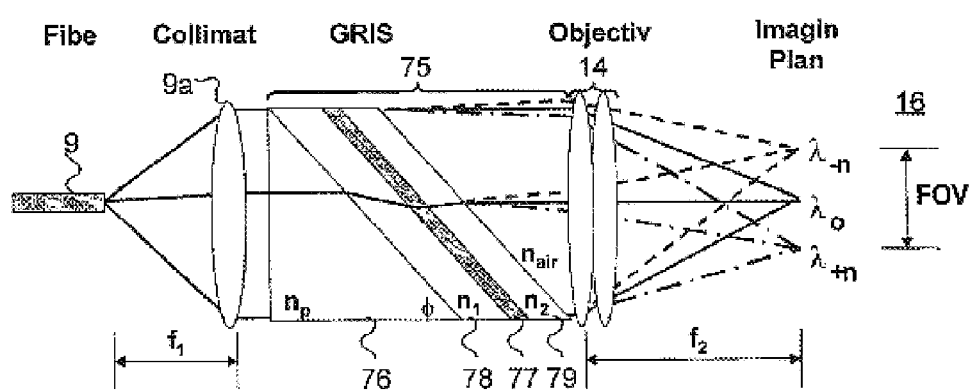
FIG. 10 is a diagram illustrating the forward-imaging SECM probe of FIG. 9A.

The forward imaging design of probe/catheter 40 (FIG. 9A) may present a challenge of aligning the beam path with the axis of the probe/catheter 40 in the presence of a grating that may inherently deflect the beam (e.g., grating 12, which may be enclosed in optics and controls housing 45 within inner core 55). The beam path alignment may be achieved using a grating prism pair 75, also known as GRISM (FIG. 10). As shown in FIG. 10, GRISM 75 may include a prism 76 (made of a material characterized by refractive index $n_p$ and having an angled surface defined by $\Phi$), a grating 77, and materials 78 and 79 characterized by refractive indexes $n_1$ and $n_2$, respectively. For this application a transmission mode GRISM 75 is preferred. (FIG. 10) While blazed and binary gratings can be used, research has shown that the preferred embodiment includes a holographic grating fixed to the angled prism face. The holographic grating may be of any type, including, a Dickson grating, and the like. Distances f1 and f2 shown in FIG. 10 may have a predetermined relationship with each other and/or one or more characteristics/parameters of GRISM 75 (e.g., $n_p$, $\Phi$, $n_1$, $n_2$, dimensions of GRISM 80, and so forth, which may be predetermined according to design and material). In accordance with an embodiment of the invention, the prism of GRISM 75 may be made of silicon, other high refractive index materials, and the like. When using high refractive index materials, appropriate anti-reflection coatings at all refractive index interfaces may be used to increase transmission and avoid deleterious back-reflections.

Thus, the optical components shown in FIG. 10, including GRISM 75, may be the optical components enclosed in optics and controls housing 45 within inner core 55 of forward-imaging probe/catheter 40 shown in FIG. 9A. To accommodate for the large deflection angles, high index of refraction materials may be required. Table 1 shows a list of design parameters for some of the possible designs at different wavelengths. The design options are and depend on the allowed tradeoffs between field of view, resolution and availability of gratings and prisms.

TABLE 1

Possible Design Parameters for a Forward Imaging Probe at Different Wavelenghts.

| Design Parameters | | | | | |
|---|---|---|---|---|---|
| Numerical Aperture | | | 0.9 | | |
| Clear Aperture (mm) | | | 4.6 | | |
| Bandwidth (nm) | | | 110 | | |
| Wavelength (nm) | 632 | 800 | 1046 | 1300 | 1500 |
| Grating Frequency (lines/mm) | 1200 | 1200 | 1100 | 1000 | 950 |
| Prism Index of refraction | 2.00 | 2.10 | 2.50 | 2.75 | 2.75 |
| Design Results | | | | | |
| Field of View (μm) | 328 | 328 | 325 | 328 | 327 |
| Diffraction Limited Resolution (μm) | 0.184 | 0.211 | 0.391 | 0.565 | 593 |
| Bandwidth Limited Resolution (μm) | 0.309 | 0.391 | 0.511 | 0.636 | 733 |
| Axial Resolution (μm) | 1.55 | 1.957 | 2.559 | 3.18 | 3.669 |

It is noted that the design parameters may be within a range of ±5% of those listed in Table 1 above.

Figure 11:
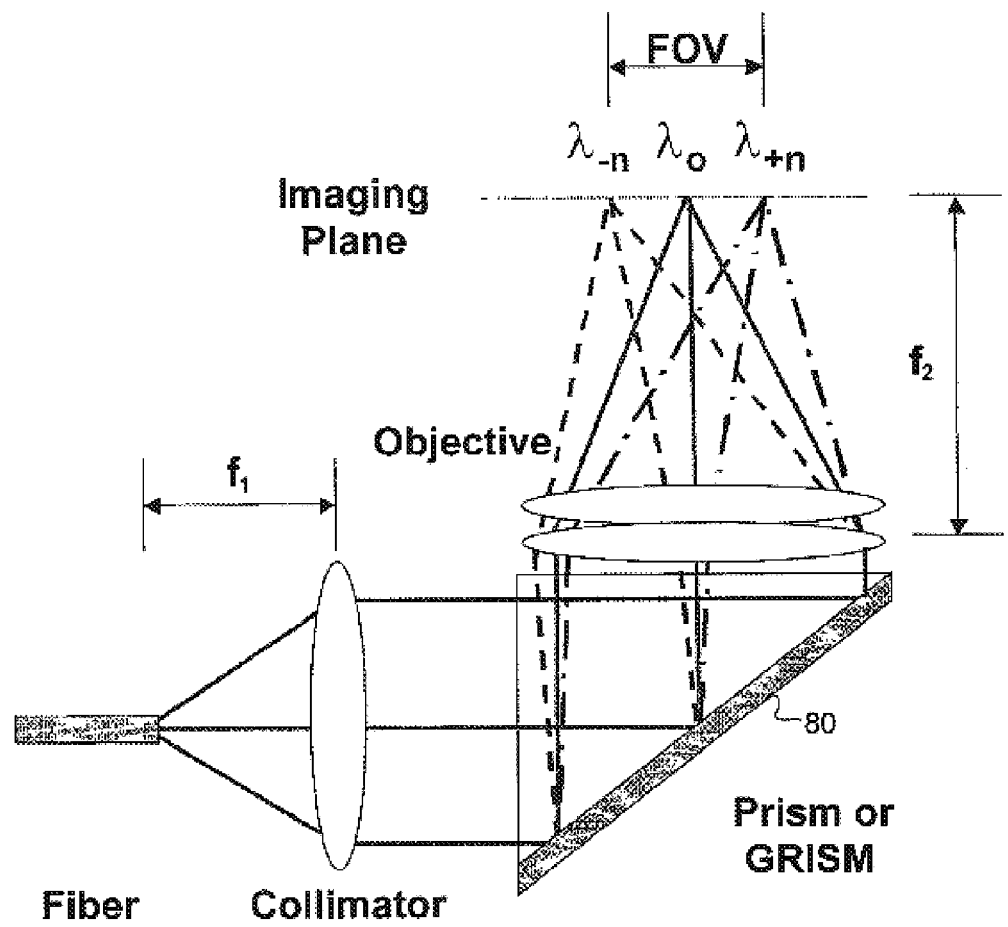
FIG. 11 is a diagram showing an angle-imaging SECM probe in accordance with an embodiment of the invention.

Another possible design allows SECM imaging at different angles. This may be preferable when imaging small lumens or complicated or uneven surfaces such as those of the mouth. As shown in FIG. 11, a reflective prism or reflective GRISM 80 (for simplicity hereinafter referred to as GRISM 80) can be used to allow complete control over the imaging angle of the device (e.g., probe/catheter 42 of FIG. 9B). Distances f1 and f2 shown in FIG. 11 may have a predetermined relationship with each other and/or one or more characteristics/parameters of GRISM 80 (e.g., angle of reflection, dimensions, and so forth, of GRISM 80 which may be predetermined according to design and material). In accordance with an embodiment of the invention, GRISM 80 may be made of silicon, other high refractive index materials, and the like. When using high refractive index materials, appropriate anti-reflection coatings at all refractive index interfaces are necessary to increase transmission and avoid deleterious back-reflections.

To achieve two-dimensional imaging, the slow axis can be scanned in a variety of ways. One possibility is to rotate the inner core 55 of the probe by, say, rotator 50 to image either circular (e.g., for forward-imaging probe 40 as shown in FIG. 12A) or cylindrical sections (e.g., for side-imaging probe 42 as shown in 13A). The probe can also be configured to linearly translate and obtain images from planes parallel to the axis of the probe (e.g., by sliding inner core 55 using an actuator 50 as shown in FIG. 13B). Another mode of operation may be to deflect the beam using mechanical or optical techniques, including, but not limited to, piezo-electric, electro-optic, acousto-optic, mechanical, electromagnetic or pneumatic devices 85. (FIG. 12B)

Figure 14:
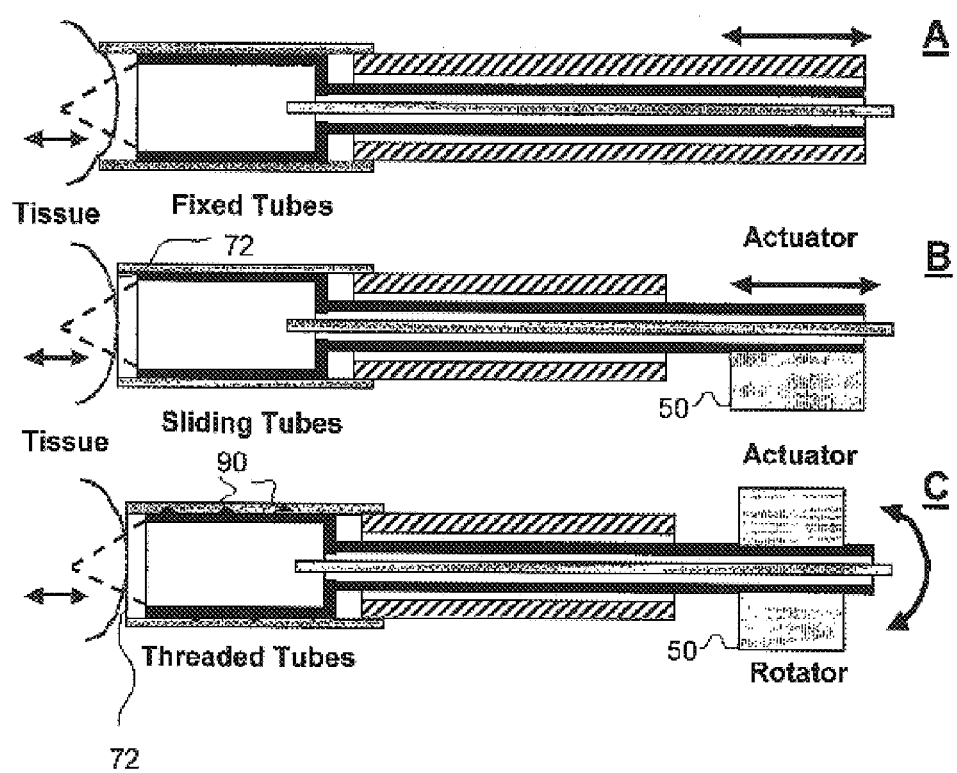
FIGS. 14A, 14B and 14C illustrate the focus adjustment for the forward-imaging probe of FIG. 9A in accordance with respective embodiments of the invention.
Figure 15A:
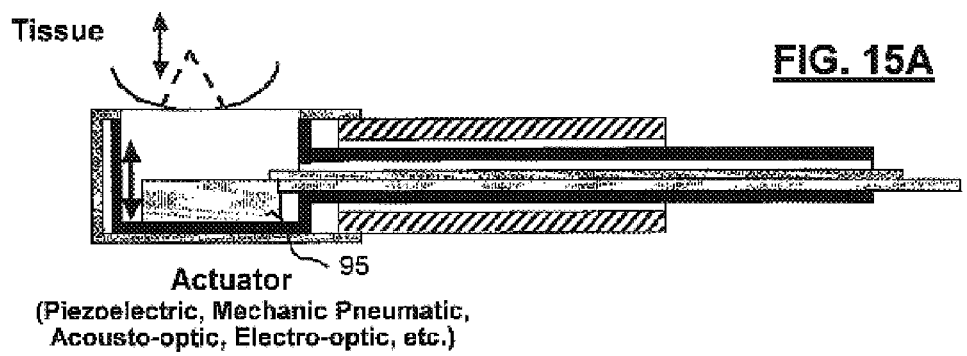
FIGS. 15A and 15B illustrate the focus adjustment for the side-imaging probe of FIG. 9B in accordance with respective embodiments of the invention.
Figure 15B:
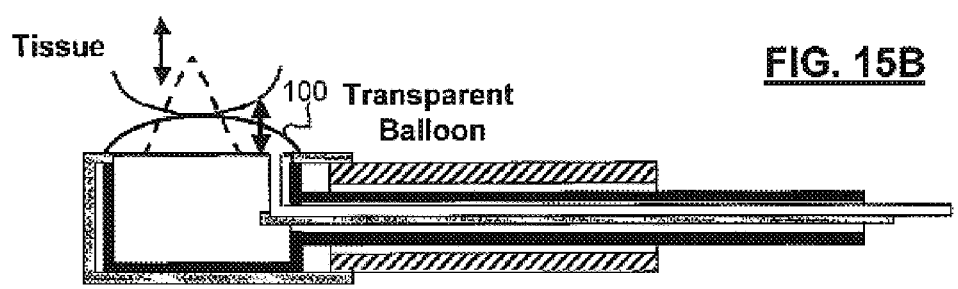

The focal plane of the probe can also be adjusted to allow visualization of different layers within the tissue under investigation. In a forward imaging catheter (40), this can be done either by applying variable pressure against an elastic spacer placed in front or behind the imaging window (FIG. 14A), by linear translating the inner core with respect to the outside sheath and the imaging window 72 (FIG. 14B), or by rotating the inner core with threaded inner optics assembly 90 against an also threaded outside sheath and imaging window 72. (FIG. 14C). For a side imaging probe (42) the focal plane can be adjusted by a translator 95 (FIG. 15A), possibly mechanical, pneumatic or piezoelectric, or a balloon 100 external to the probe. (FIG. 15B)

Figure 16:
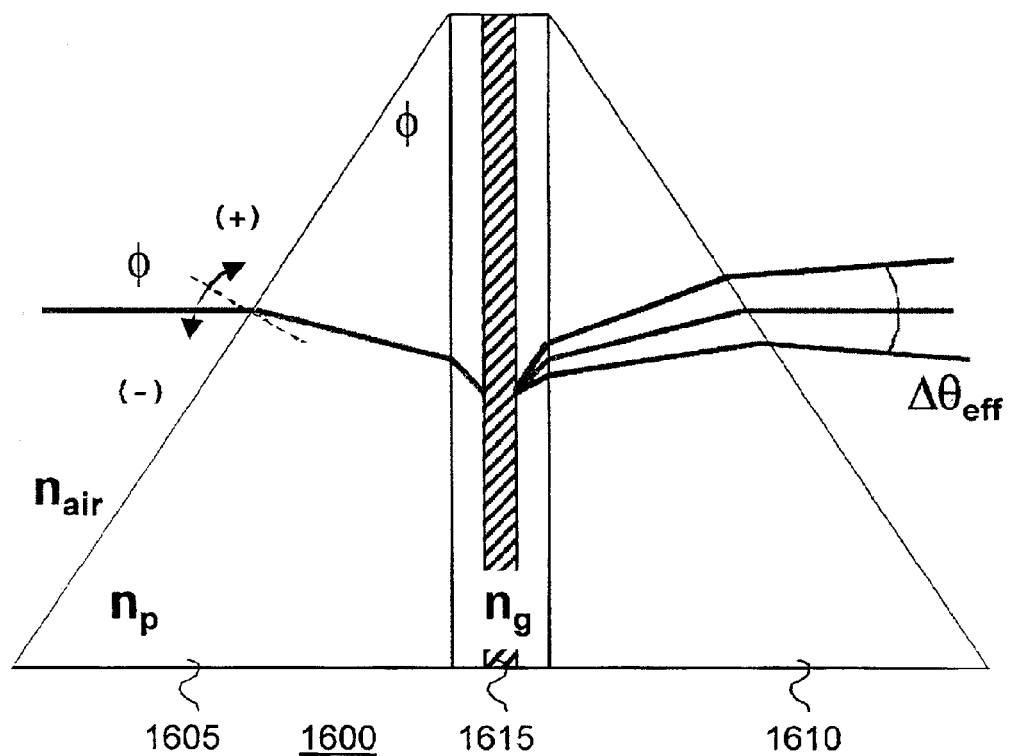
FIG. 16 is a diagram illustrating a dual prism grating prism pair (or "GRISM") according to an embodiment of the invention.

Another GRISM design that appears well suited for forward imaging application is the symmetrical dual prism design 1600 (FIG. 16). As shown in FIG. 16, dual prism GRISM 1600 may include prisms 1605 and 1610 and a grating 1615. In accordance with an embodiment of the invention, prism 1605 may be made of a material characterized by a refractive index $n_p$ and may include an angled surface defined by $\Phi$. Grating 1615 may be made of a material characterized by a refractive index $n_g$. Grating 1615 may be a holographic grating. Dual prism GRISM 1600 may be symmetrical in that prism 1610 may also be made of a material characterized by refractive index $n_p$ and may also include an angled surface defined by $\Phi$. This allows the beam in and out of the grating 1615 to be at the same angle (Littrow's angle) thus making the design very efficient at both polarizations. One or more characteristics/parameters of the dual prism GRISM 1600, e.g., $n_p$, $n_g$, $\Phi$, and so forth, may be predetermined according to the needs of the application. The air adjacent the dual prism GRISM 1600, i.e., $n_{air}$, may be replaced with a material having a different refractive index n. Grating 1615 may also be separated from prisms 1605 and 1610 by a material having a predetermined n. Different choices of prism material (e.g., silicon, other high refractive index materials, and the like) and, therefore, prism angle allow to a large extend customization of the output beam spread ($\Delta\theta$) to match the device's requirements. To minimize beam clipping, the total length of the dispersive optical element, while maximizing dispersion, high index of refraction materials may be required for the prism. Table 2 shows a list of design parameters for some of the possible designs at different wavelengths. The key advantage to this configuration is the ability to achieve high spectral dispersion while maintaining forward beam propagation.

TABLE 2

Parameters for a dual-prism GRISM using a Dickson holographic transmission grating and silicon prisms. The clear aperture is 9 mm Λ lines/mm, EFL Effective focal length, φ grating incident angle, Δθ$_{eff}$ - objective illumination angle, FOV - field of view, Δr - wavelength encoded resolution. All non-angle units are in micrometers (μm).

| Λ | EFL | φ | Δθ$_{eff}$ | FOV | Δr | Clipping |
|---|---|---|---|---|---|---|
| 700.000 | 3.000e3 | 10.428 | 4.544 | 238.055 | 0.447 | 0.212e3 |
|  | 3.750e3 |  |  | 297.568 | 0.558 |  |
|  | 4.500e3 |  |  | 357.082 | 0.670 |  |
|  | 5.250e3 |  |  | 416.595 | 0.781 |  |
|  | 6.000e3 |  |  | 476.109 | 0.893 |  |
| 800.000 | 3.000e3 | 11.921 | 5.232 | 274.154 | 0.450 | 0.277e3 |
|  | 3.750e3 |  |  | 342.693 | 0.563 |  |
|  | 4.500e3 |  |  | 411.231 | 0.675 |  |
|  | 5.250e3 |  |  | 479.770 | 0.788 |  |
|  | 6.000e3 |  |  | 548.308 | 0.900 |  |

TABLE 2-continued

Parameters for a dual-prism GRISM using a Dickson holographic transmission grating and silicon prisms. The clear aperture is 9 mm Λ lines/mm, EFL Effective focal length, φ grating incident angle, Δθ$_{eff}$ - objective illumination angle, FOV - field of view, Δr - wavelength encoded resolution. All non-angle units are in micrometers (μm).

| Λ | EFL | φ | Δθ$_{eff}$ | FOV | Δr | Clipping |
|---|---|---|---|---|---|---|
| 933.333 | 3.000e3 | 13.914 | 6.176 | 323.684 | 0.455 | 0.376e3 |
|  | 3.750e3 |  |  | 404.605 | 0.569 |  |
|  | 4.500e3 |  |  | 485.525 | 0.683 |  |
|  | 5.250e3 |  |  | 566.446 | 0.797 |  |
|  | 6.000e3 |  |  | 647.367 | 0.911 |  |
| 1120.000 | 3.000e3 | 16.708 | 7.558 | 396.324 | 0.465 | 0.540e3 |
|  | 3.750e3 |  |  | 495.405 | 0.581 |  |
|  | 4.500e3 |  |  | 594.486 | 0.697 |  |
|  | 5.250e3 |  |  | 693.567 | 0.813 |  |
|  | 6.000e3 |  |  | 792.648 | 0.929 |  |

It is noted that the design parameters may be within a range of ±5% of those listed in Table 2 above. It is further noted that the preferred embodiment may include the following parameters listed in Table 3.

TABLE 3

Preferred parameters for a dual-prism GRISM using a Dickson holographic transmission grating and silicon prisms.

| Λ | EFL | φ | Δθ$_{eff}$ | FOV | Δr | Clipping |
|---|---|---|---|---|---|---|
| 1120.000 | 5.250e3 | 16.708 | 7.558 | 693.567 | 0.813 | 0.540e3 |

It is yet further noted that the preferred design parameters may be within a range of ±5% of those listed in Table 3 above.

Figure 17:
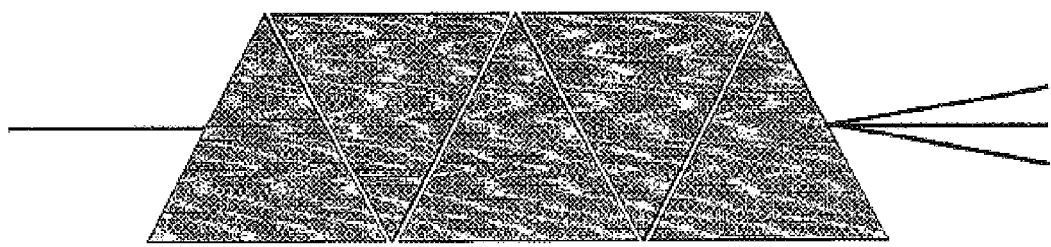
FIG. 17 illustrates a multiple prism dispersion element embodying the invention.

Another design for forward imaging is a series of prisms (FIG. 17). Although this setup suffers from less dispersive power compared to grating designs it is relatively simple and can be fabricated to a very small size.

Figure 18A:
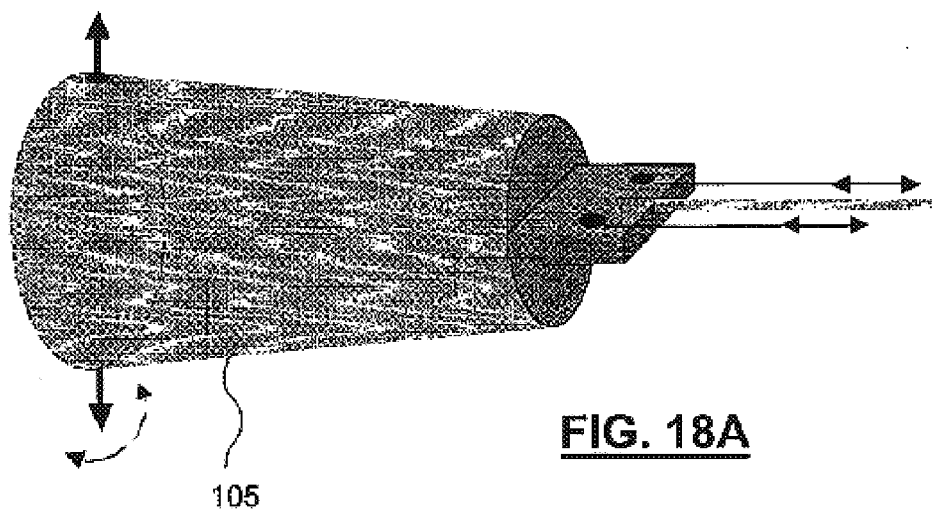
FIGS. 18A and 18B are diagrams illustrating slow scanning mechanisms by: (a) linear transduction; and (b) rotation with cam or lever mechanism, according to respective embodiments of the invention.
Figure 18B:
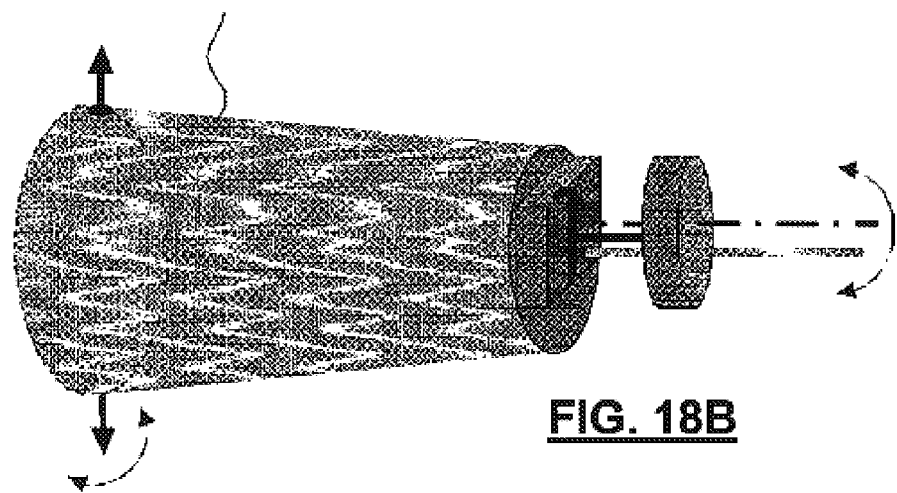

Scanning the slow (y) axis can also be implemented by tilting the fiber 9 and collimator 9a combination. This can be achieved by pivoting the cone 105 that holds the fiber/collimator assembly by a number of ways, including push-pull (FIGS. 18A and 19A) and rotating an off-axis lever (FIGS. 18B and 19B). Both these schemes can be implemented with transducers in-line with the fiber-collimator assembly, thus not increasing the overall diameter of the device.

Another way to scan (the fiber-collimator, a fiber or even the objective) is by using a cylindrical piezoelectric bi-layer. This bimorph has the property of expanding its diameter when supplied with voltage thus effectively scanning the object attached to the free end (FIGS. 20A, 20B, and 20C). Advantages of this design may include its simplicity and high torque capability, but the design may require high voltage and for small diameters the expansion may be limited by the physical properties of piezoelectric material available today.

The systems, methods, apparatuses, and techniques of the present invention described above may be used for intraoperative tissue identification. Using a probe (8, 40, or 42) embodying features of the present invention, a surgeon may be able to obtain information on tissue type during an operation, thus reducing the time needed to perform the operation and improving the outcome thereof. Time savings occurs when during the operation, the surgeon encounters tissue of unknown type. An example is identification of the parathyroid glands during parathyroidectomy and thyroidectomy. In this type of operation, it is difficult to identify the parathyroid (they are small and have an inconsistent anatomic location) and often other tissues are mistakenly thought to be parathyroid, resulting in accidental removal or damage of the parathyroid gland (in thyroidectomy surgeries) or in removal of muscle, fat or lymph node (in parathyroidectomy surgeries) and resultant increase in operation time due to frozen section processing. A hand held probe (such as a SECM device embodying features of the present invention) could be used in these instances to identify the parathyroid gland and avoid incorrect surgical removal of tissue of the patient. This problem exists in other surgeries also, but is of particular importance in head and neck surgeries due to the complex anatomy in this anatomic region. A device embodying features of the present invention may be used to identify any tissue type, including, thyroid tissue, fetal tissue, and the like. Moreover, for all surgeries, the capabilities provided by a system according to the present invention may decrease operation time just by providing the surgeon with more information prior to cutting.

From the foregoing description, it will be apparent that the invention provides a confocal microscopy system which (a) is compact, optical fiber-based, capable of enabling confocal microscopy through a flexible catheter or endoscope; (b) is fast-scanning which takes place external to the probe; (c) allows phase information to be retrieved; and (d) provides a number of resolvable points proportional to the bandwidth of the source and the beam diameter on the grating. Variations and modifications in the herein described confocal microscopy system and probe/catheter in accordance with the invention will undoubtedly suggest themselves to those skilled in the art. Accordingly, the foregoing description should be taken as illustrative and not in a limiting sense. Thus, although preferred embodiments of the present invention and modifications thereof have been described in detail herein, it is to be understood that this invention is not limited to these embodiments and modifications, and that other modifications and variations may be effected by one skilled in the art without departing from the spirit and scope of the invention as defined by the appended claims.

What is claimed is:

1. An apparatus movable into a body region of interest for use with a confocal microscope system, said apparatus comprising:
    means for illuminating the body region with a confocal spectrum of light extending along one non-longitudinal dimension; and
    means for obtaining an image of the body region by moving said spectrum along another dimension and measuring the reflected confocal spectrum of said light.

2. An apparatus for confocally imaging tissue, comprising:
    an input for receiving light from a light source;
    a light dispersing unit connected to the input for producing a confocal spectrum of said light;
    a focusing unit operable to focus said confocal spectrum at the tissue along a non-longitudinal dimension; and
    a light detecting unit operable to detect returned light from the tissue in accordance with a spectrum of said returned light to provide an image representing the tissue.

3. The apparatus of claim 2, wherein said input comprises an optical fiber for transmitting said light.

4. The apparatus of claim 2, wherein said light dispersing unit comprises a grating.

5. The apparatus of claim 2, wherein said light dispersing unit comprises a light deflecting unit for deflecting said confocal spectrum to said dimension.

6. The apparatus of claim 5, wherein said light deflecting unit comprises a prism.

7. The apparatus of claim 6, wherein said light dispersing unit comprises a grating.

8. The apparatus of claim 7, wherein said grating is a holographic grating.

9. The apparatus of claim 7, wherein said grating is fixed to an angled face of said prism.

10. The apparatus of claim 6, wherein said prism is a reflective prism.

11. The apparatus of claim 5, wherein said light deflecting unit comprises a grating prism pair.

12. The apparatus of claim 11, wherein said light deflecting unit comprises a dual prism grating prism pair.

13. The apparatus of claim 2, further comprising an adjustment unit operable to adjust said confocal spectrum at the tissue.

14. The apparatus of claim 13, wherein said adjustment unit moves said confocal spectrum in another direction along a second dimension.

15. The apparatus of claim 13, wherein said adjustment unit adjusts said focusing unit.

16. The apparatus of claim 13, wherein said adjustment unit comprises one or more of a rotator, an actuator, a beam deflector, and a balloon.

17. The apparatus of claim 13, wherein said adjustment unit adjusts said input.

18. The apparatus of claim 17, wherein said input comprises a fiber/collimator assembly.

19. The apparatus of claim 18, wherein said adjustment unit comprises one or more of a linear transduction mechanism, a rotational cam mechanism, and a rotational lever mechanism for moving said fiber/collimator assembly.

20. The apparatus of claim 13, wherein said adjustment unit comprises a circular piezoelectric bimorph.

21. The apparatus of claim 13, wherein said adjustment unit moves said confocal spectrum around an axis that extends in another direction.

22. A method of identifying one or more targets for an operation in tissue, comprising using the system according to claim 2, and identifying the one or more targets in accordance with the returned light.

23. The method of claim 22, wherein the tissue is thyroid tissue.

24. The method of claim 22, wherein the tissue is fetal tissue.

25. The method of claim 22, wherein the tissue is muscle tissue.

26. The method of claim 22, wherein the tissue is fat tissue.

27. The method of claim 22, wherein the tissue is lymph node tissue.

28. A method of identifying one or more targets for an operation in tissue, comprising using the apparatus according to claim 2, and identifying the one or more targets in accordance with the image representing the tissue.

29. The method of claim 28, wherein the tissue is thyroid tissue.

30. The method of claim 28, wherein the tissue is fetal tissue.

31. The method of claim 28, wherein the tissue is muscle tissue.

32. The method of claim 28, wherein the tissue is fat tissue.

33. The method of claim 28, wherein the tissue is lymph node tissue.

34. A system for confocally imaging tissue comprising:

a light source operable to produce light;

a light dispersing unit connected to the light source for producing a confocal spectrum of said light;

a focusing unit operable to focus said confocal spectrum at the tissue along a non-longitudinal dimension ; and a light detecting unit operable to detect returned light from the tissue in accordance with a spectrum of said returned light to provide an image representing the tissue.

35. A method of identifying one or more targets for an operation in tissue, comprising using the apparatus according to claim 34, and identifying the one or more targets in accordance with the image representing the tissue.

36. The method of claim 35, wherein the tissue is thyroid tissue.

37. The method of claim 35, wherein the tissue is fetal tissue.

38. The method of claim 35, wherein the tissue is muscle tissue.

39. The method of claim 35, wherein the tissue is fat tissue.

40. The method of claim 35, wherein the tissue is lymph node tissue.

41. A confocal microscope system which comprises a probe movable into a body region of interest, said probe having means for illuminating said region with a confocal spectrum of light extending along one non-longitudinal dimension, means for obtaining an image of the region of the specimen by moving said spectrum along another dimension and measuring the reflected confocal spectrum of said light.

42. An apparatus movable into a body region of interest for use with a confocal microscope system, said apparatus comprising:

an illumination unit operable to illuminate the body region with a confocal spectrum of light extending along one non-longitudinal dimension; and an image detecting unit coupled to said illumination unit, said image detecting unit operable to obtain an image of the body region by moving said spectrum along another dimension and measuring the reflected confocal spectrum of said light.

43. A method of identifying one or more targets for an operation in a body region, comprising using the apparatus according to claim 42, and identifying the one or more targets in accordance with the image of the body region.

44. The method of claim 43, wherein the body region comprises thyroid tissue.

45. The method of claim 43, wherein the body region comprises fetal tissue.

46. The method of claim 43, wherein the body region comprises muscle tissue.

47. The method of claim 43, wherein the body region comprises fat tissue.

48. The method of claim 43, wherein the body region comprises lymph node tissue.

* * * * *